(12) United States Patent
Patch

(10) Patent No.: US 6,317,478 B1
(45) Date of Patent: Nov. 13, 2001

(54) METHOD AND APPARATUS FOR IMAGING BASED ON CALCULATED INVERSION VALUES OF CONE BEAM DATA

(75) Inventor: Sarah Kathryn Patch, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/475,740

(22) Filed: Dec. 30, 1999

(51) Int. Cl.[7] .......................................................... A61B 6/03
(52) U.S. Cl. .................................. 378/4; 378/901
(58) Field of Search ................... 378/4, 15, 901

(56) References Cited

U.S. PATENT DOCUMENTS

| | | | |
|---|---|---|---|
| 5,446,776 | 8/1995 | Tam | 378/4 |
| 5,465,283 | 11/1995 | Tam | 378/4 |
| 5,901,196 | * 5/1999 | Sauer et al. | 378/4 |
| 6,233,303 | * 5/2001 | Tam | 378/4 |

* cited by examiner

Primary Examiner—David V. Bruce
(74) Attorney, Agent, or Firm—Donald S. Ingraham; Christian G. Cabou

(57) ABSTRACT

A method and apparatus for imaging an object by applying imaging energy from a source to the object such that a cone beam of imaging energy (40) that has passed through the object is detected by a detector. In contrast to known methods, direct x-ray inversion of the cone beam measurements is made, where the inversion includes a backprojection step that precedes the filtering step. The inverted cone beam measurements are backprojected on the fly, thereby reducing lag time between the end of data collection and image generation to the time required to perform a fast Fourier-based filter of the backprojected data.

16 Claims, 5 Drawing Sheets

METHOD AND APPARATUS FOR IMAGING BASED ON CALCULATED INVERSION VALUES OF CONE BEAM DATA

BACKGROUND OF THE INVENTION

The present invention relates generally to computed tomography (CT) imaging techniques; and more particularly, to the backprojection of the attenuation data acquired during a scan to form an image.

In a computed tomography system, an x-ray source projects a cone beam that passes through an object being imaged, such as a medical patient, and impinges upon a two dimensional (2D) array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce a transmission profile.

U.S. Pat. No. 5,446,776 describes a technique employing a conventional CT system employing cone beam geometry for 3D imaging using a cone beam x-ray source and a 2D area detector. The source and detector array in the system are rotated on a gantry preferably over a 360° angular range, either by moving the cone beam x-ray source in a scanning circle about the object while keeping the 2D array detector fixed with reference to the cone beam x-ray source, or by rotating the object while the x-ray source and detector remain stationary. A group of x-ray attenuation measurements obtained from the detector array at a given angle is referred to as a "view". A "scan" of the object comprises a set of views made at different angular orientations during one revolution of the x-ray source and detector.

Different data processing techniques have been employed to present imaging data in manners that are helpful to the user e.g., providing tomographic information and the lie. Typically such processing, particularly for generation of 3 dimensional (3D) images, is computationally intensive, resulting in slow response due to lengthy processing time or requiring significant computational resources, with attendant cost, or both.

SUMMARY OF THE INVENTION

In an exemplary embodiment of the method of the invention, an object is imaged by applying imaging energy from a source to the object. Imaging energy that has passed through the object is detected by a detector. The object is scanned with the imaging energy such that the detector collects cone beam measurements. Direct x-ray inversion of the cone beam measurements is made, followed by backprojection and filtering. In contrast to known methods in which the filtering step precedes the backprojection step, in the present invention, the backprojection step advantageously precedes the filtering step. The inverted cone beam measurements are backprojected on the fly, thereby reducing the lag time between the end of data collection and image generation to the time required to perform a fast Fourier-based filter of the backprojected data.

An exemplary embodiment of the system of the invention includes a source for applying imaging energy to the object. A detector detects imaging energy that has passed through the object. A positioner scans the object with the imaging energy such that the detector collects cone beam measurements. An inversion calculator performs direct x-ray inversion of the cone beam measurements. A backprojection and filtering calculator calculates the backprojection and filtering of the inverted cone beam measurements. An image supplier supplies an image of the object based on the measured image data and the backprojected, filtered inverted cone beam measurements.

DETAILED DESCRIPTION

Figure 1:
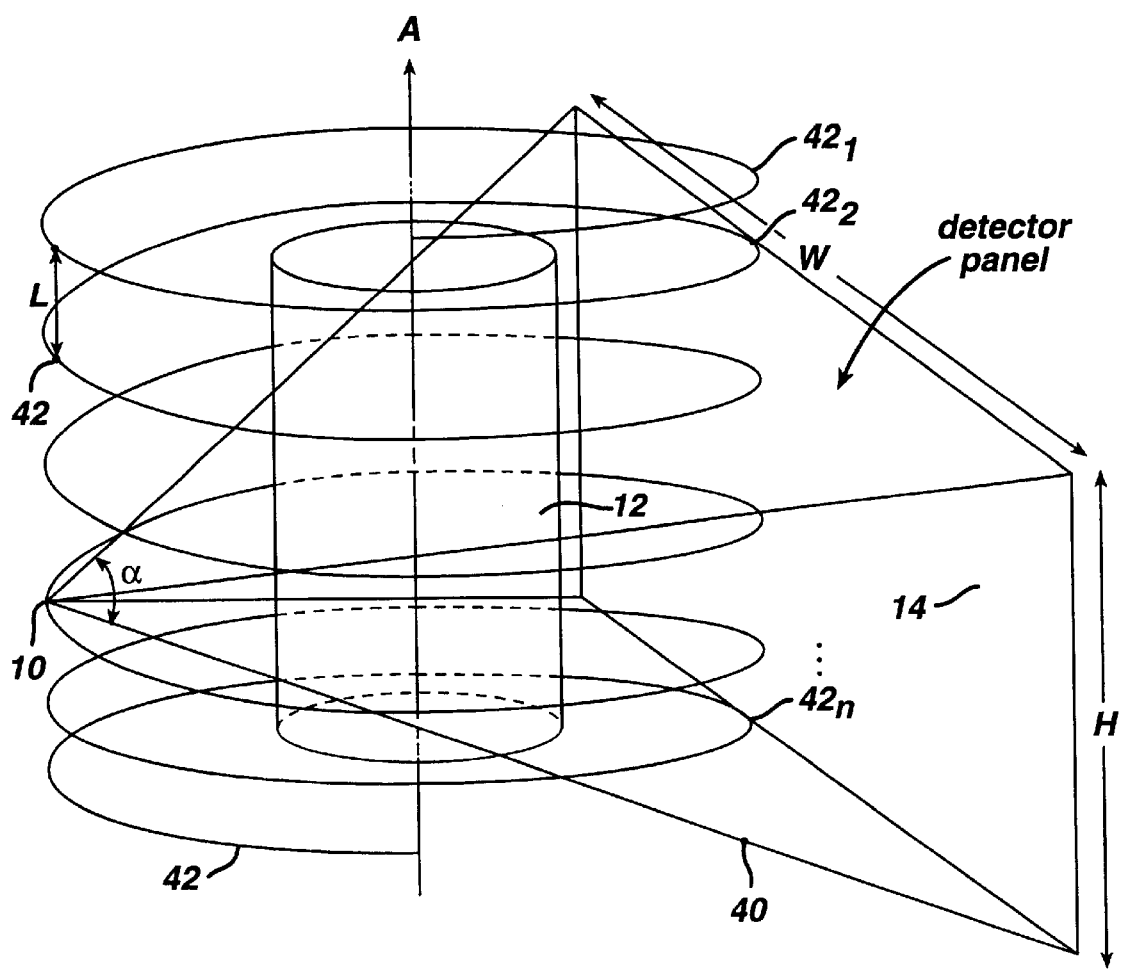
FIG. 1 is a simplified illustration of a cone beam path with respect to an object to be imaged and a detector panel for receiving the cone beam.

Information relating to beam reconstruction using a 2D area detector is provided herewith to assist in presentation of the present invention. FIG. 1 is a simplified schematic illustration of an imaging cone beam path illustrated in FIGS. 1 and 2, emphasizing a generally helical path generated by source 10. Object 12 may be stationary during the imaging process in which source 10 and detector 14 together are moved axially as they are rotated with respect to object 12. In the alternative, object 12 may be moved linearly along an axis while source 10 and detector 14 are together rotated. Alternatively, body 12 may be rotated while being moved axially with respect to a fixed source 10 and detector 14. FIG. 1, taken in conjunction with FIGS. 2 and 3, are used to explain basic concepts used by the present invention, before presenting more complex mathematical explanations used for implementation of the invention.

In the simplified schematic illustration of FIG. 1, a source 10 applies imaging energy beams 40 which passes through object 12 having a longitudinal axis A. The beams 40 strike a detector 14, shown as a two dimensional array having a detector height H and a detector width W, and positioned to the other side of object 12 from source 10. Energy beams 40 are shown in outline for ease of illustration, but as readily appreciated, the actual output of source 10 is a cone beam which may be considered as individual rays corresponding to the resolution of the area detector 14. The energy beam of the energy source 10 moves along a helical path 42 about axis A relative to object 12, as a result of relative movement of source 10 and object 12, and radiates energy beam 40 at an effective cone angle $\alpha$ along a helical scan path. The helical path 42 has a pitch L, which corresponds to a degree of "tightness". Individual turns of path 42 are represented by areas $42_1, 42_2, \ldots 42_n$.

Figure 2:
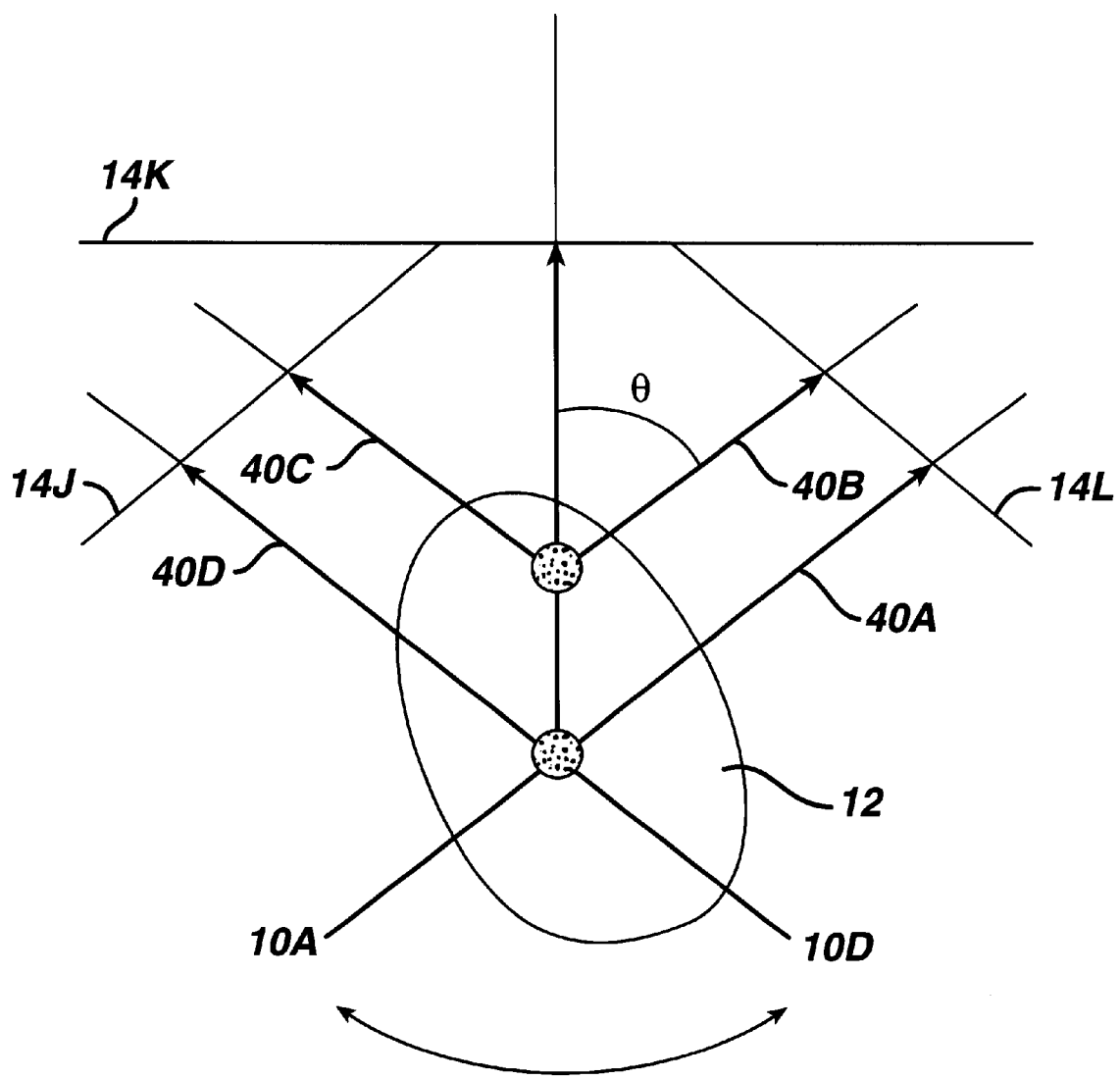
FIG. 2 is a simplified illustration of a cone beam.

FIG. 2 illustrates a simplified representation comprising a plurality of energy beams 40 of a cone beam, shown for example, as beams $40_a \ldots 40_n$ projecting from a point source 10 (not shown) in FIG. 2, moving in synchronization with the detector (not shown) with respect to the object 12 being imaged. The source 10 moves through corresponding successive positions $10_a \ldots 10_n$ and the detector 14 moves through successive positions represented by lines $14_j \ldots 14_n$. A complete rotation of source 10 and detector 14 together through a helix portion $42_i$ is a "scan". For clarity of illustration, only two source positions 10A and 10D are shown. For example, position 10A results in emission of an energy beam 40A, which is detected by detector 14 at a corresponding location 14L. All energy beams 40A . . . $40_n$ have similar corresponding source positions 10A . . . $10_n$, and respective detector positions 14A . . . $14_n$. Views of the object are acquired at selected angles θ around object 12.

Figure 3:
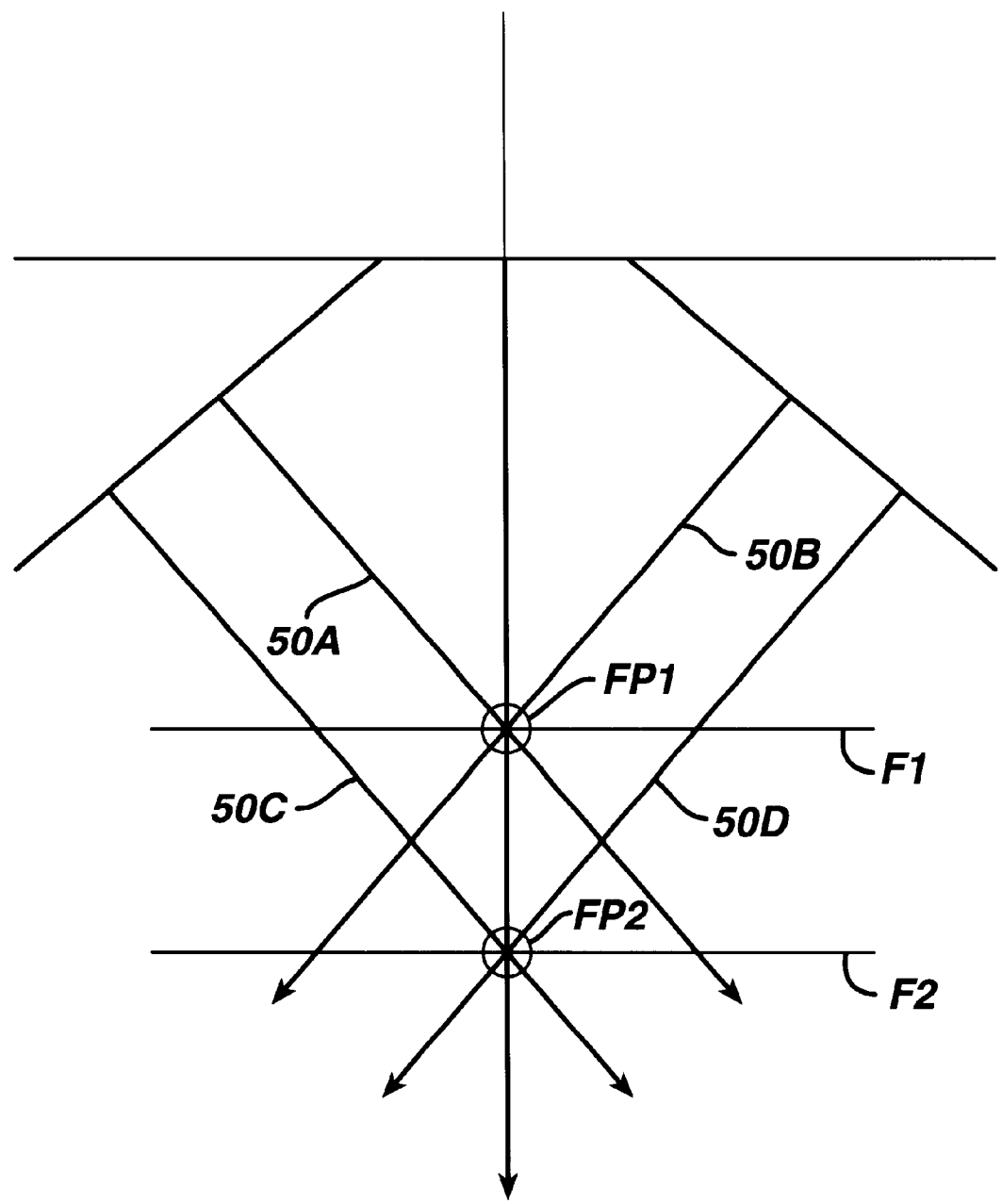
FIG. 3 is a simplified illustration of backprojected images derived from the cone beam illustrated in FIG. 1.

FIG. 3 illustrates backprojection of the collected views obtained in the system illustrated in FIG. 2 into an image volume to produce an image with a tomographic effect. A mathematical combination by means of known reconstruction algorithms of the views acquired from a complete scan at a limited number of angles θ around the object 12 results in a tomographic image segment when backprojected into an image volume. Image data representing structures from all depths contribute to the signal for a particular depth. However, only image data representing structures within that particular depth will be in focus, thereby producing a "higher" signal. Image data representing structures originating from a different depth will be smeared out over a larger area, thus producing a "lower" signal. For example, focus line F1 illustrates a high signal for backprojected image values 50A and 50B, which cross at or near the focal point FP1 along line F1, while values 50C and 50D mathematically combine to form a lower signal, i.e., they are out of focus. Similarly, focus line F2 illustrates a higher signal representing the mathematical combination of values 50C and 50D, which crosses at or near the focal point FP2, while values 50A and 50B combine to yield a lower signal value. For any focal plane, a set of functions $f_i$ describing a particular view is desired.

A complete data set for exact reconstruction (i.e., providing a three-dimensional image) is obtained by measuring a sufficient set of line integrals (not shown) corresponding to respective beams 40, as source 10 is scanned in helical trajectory 42. In practicality, data representation is limited by helical pitch L, cone angle α and detector dimensions H and W. For example, a continuously sampled helical path directly measures complete x-ray data in the limit, as the helical pitch L approaches zero, the cone half angle approaches π/2 and as the detector dimensions H and W approach infinity.

Figure 4:
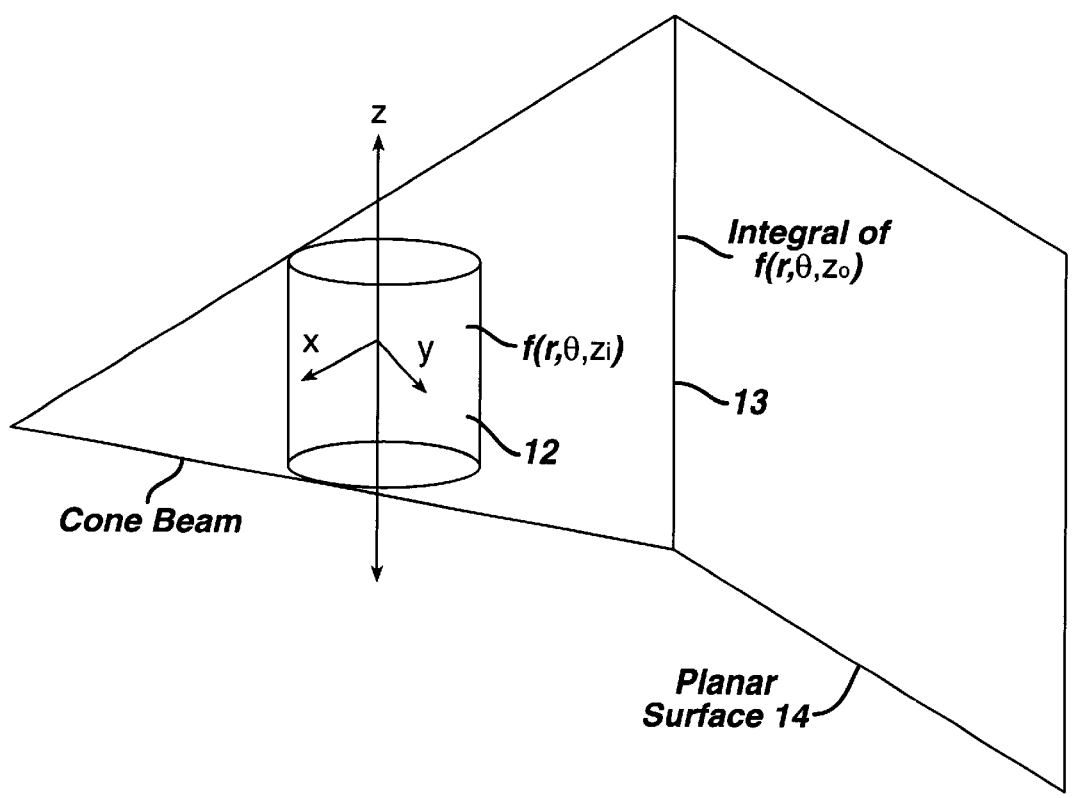
FIG. 4 a simplified illustration of a line integral of a projection of the function illustrated in FIG. 1 onto a planar surface.

Referring to FIG. 4, an image representation of an object 12 is defined by the object's x-ray attenuation coefficient f(x,y,z) describing object 12. A coordinate transformation of f(x,y,z) from Cartesian to polar coordinates is shown as f(r,θ, $z_i$) represented by cylinder 12. A line integral of a projection of the function f(r,θ, $z_i$) onto a planar surface is represented by line 13. The integral of the function f(r,θ, $z_i$) over the radial direction is shown as X(θ)=.intg.f(r,θ, $z_0$)dr, which corresponds to the measured cone beam projection data. The measured cone beam projection data, which are values, i.e., data, actually read from the detector 14 during each scan, thus corresponds to a line integral of the unknown function f(r,θ, $z_i$) over the radial direction. The objective is to determine the unknown function and its value for all points (r,θ, $z_i$) representing object 12. The collection of such values is an image representation of object 12 in three dimensions.

Known 3D CT imaging techniques to determine the unknown function, also written generally as $f_i$ for all points i, generally use a Radon transform approach to calculate a reconstructed image $f_i$ forming the desired tomographic image. The technique begins with obtaining a set of line integrals in a plane that are measured for a number of angles. This set of line integrals results in a set of profiles commonly referred to as the Radon transform of the object. The objective is to reconstruct a three dimensional image f(x,y,z) in the Cartesian coordinate system from its Radon transform through the use of reconstruction algorithms. One such reconstruction algorithm is the filtered backprojection technique.

U.S. Pat. No. 5,465,283 discloses the filtered backprojection technique in which the image is reconstructed from a set of views collected during one rotation. In general, steps for reconstruction include preprocessing, spatial filtering, and backprojection. Preprocessing includes a number of computational steps to correct the view data and to convert the data into line integral measurements. The resulting converted and corrected views are called "projections" Spatial filtering involves convolution of the projection data with a reconstruction filter kernel. Backprojection follows, and is a process of mapping the filtered projections into the image plane to create the actual image.

To create the image to be displayed, the filtered backprojection technique calculates the reconstructed image f(x, y) describing a particular depth and contributing to the desired tomographic image from the measured attenuation data. The measured attenuation coefficient corresponds to a line integral of the function f(x,y) over the radial direction from the radiation source to a particular detector element within the detector array. An area integral of the x-ray attenuation coefficient over a plane passing through the point provides the 3D Radon transform of an object at that point. The plane is perpendicular to the line from the origin to the particular point. When parallel beams of x-rays are applied to the object which is to be imaged, resulting line integrals of the detector data are equal to the Radon transform of the image of the object.

However, in the more complex case wherein a cone of x-rays is applied to the object to be imaged, the Radon transform is more difficult to obtain. After the Radon transform is obtained, an inverse Radon transformation is used to convert the Radon transform into a reconstructed image f(x,y,z), which is then displayed. In order to perform the Radon inversion, the Radon transform is required to reside on polar grids on a number of predetermined vertical planes containing a common axis. These requirements arise because the first part of the Radon inversion process is a 2D CT image reconstruction on each vertical plane, which takes input data in the form of Radon transforms at equally spaced angle theta and equally spaced detector spacings. A Radon circle is defined on each of the coaxial planes. Radon derivative data is calculated around the circle using the cone beam data (measured by the detector array) at each point of intersection between the Radon circle on a particular one of the planes and the radial lines for different relative source positions. This calculation is performed for each of the planes and the calculated values are stored. The calculating and storing of Radon derivative data is repeated for different relative positions of a source of the cone beam imaging energy and the object of interest until all relative positions for data acquisition have been utilized, each of the planes being used for each of the different relative positions. Upon completion of the storage of the Radon derivative data, the stored values undergo a weighting process described in U.S. Pat. No. 5,446,776 and are used to provide reconstructed image data.

This filtered backprojection technique initially produces radial first derivatives of the Radon transform, instead of the Radon transform itself. The Radon transform is derived by integrating the first derivatives, after which, the inverse Radon transform is calculated, and then reconstructed image f(x,y,z) is calculated from the inverse Radon transform. Using the technique described in U.S. Pat. No. 5,465,283, the Radon derivative data is converted to Radon transform data at the polar grid points and the result is converted into an inverse 3D Radon transformation. Subsequent conversion to reconstructed image data is according to well known techniques, for example, as described in U.S. Pat. No. 5,465,283.

Preprocessing and spatial filtering involve standard mathematical operations at a processing rate often encountered in signal processing. These steps optionally are implemented using standard digital signal processing hardware or software. Backprojection requires a much higher processing rate and requires customized, dedicated hardware for efficient implementation.

Generally speaking, the time required to build Radon data from x-ray data takes roughly half of the reconstruction time, while the other half is typically used for filtering and backprojecting using Radon-based inversion algorithms. In addition, the process of generating Radon data (plane integrals) from x-ray data (line integrals) introduces numerical errors.

Therefore, it is beneficial to significantly reduce reconstruction time by foregoing the Radon data-building step. It is also beneficial to reduce the lag time between the end of data collection and image generation by backprojecting x-ray data "on the fly".

Figure 5:
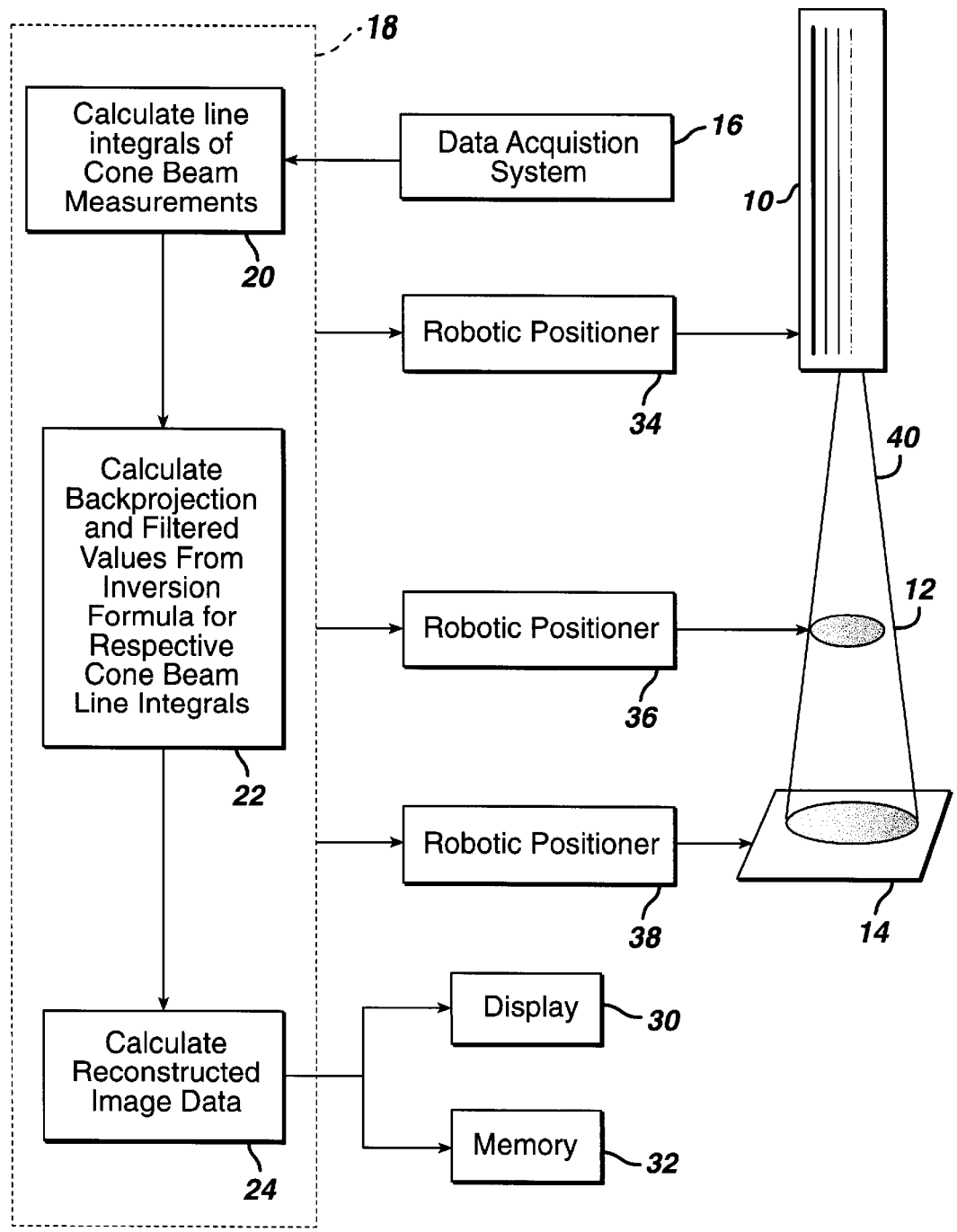
FIG. 5 is a simplified illustration of components of an imaging system and showing process steps within a processor in one embodiment of the invention.

Referring now to FIG. 5, imaging energy is applied by source 10 to object 12 and detected by detector 14. The source 10 is a cone beam x-ray source, whereas the detector 14 is an area detector such as a two dimensional array detector having an array of individual detector elements (separate elements not shown). The object 12 being imaged alternatively is a patient, an industrial part, or other object being imaged using CT.

Cone beam energy that has passed through the object 12 is converted to corresponding electrical signals and sent to a data acquisition system 16 that registers the electrical signals. System 16 sends the cone beam data to a processor 18, which is a computer adapted to perform various process steps. As used herein, "adapted to", "arranged to" and the like refer to a data processing device (e.g., a computer, application specific integrated circuit or the like) that is programmed to process data in accordance with an algorithm or process to provide an output corresponding to a desired manipulation of the data. Processor 18 converts the cone beam data into line integral measurements. Optionally, system 16 performs the conversion process and sends the line integral measurements to processor 18. Optionally, processor 18 preprocesses the signals according to known techniques including a number of computational steps to correct the view data, as necessary. Various process steps performed in processor 18 are shown in simplified form in FIG. 5. A more detailed explanation of the significance of the inversion values follows below.

At block 20, processor 18 calculates line integrals for respective cone beam measurements provided by the data acquisition system 16. At block 22, processor 18 calculates backprojection and filtered values for respective cone beam line integrals by using inversion values At block 24, processor 18 processes the complete data set of backprojection and filtered values to form an image representation of the object 12 in the usual fashion for cone beam data. The data associated with the image representation is made available for display by display 30 and storage in memory 32.

The scanning trajectory is defined by relative movements of the source 10, object 12, and detector 14 respectively controlled by robotic positioner 34, 36, and 38. Each of the robotic positioners 34, 36, and 38 are in turn controlled by processor 18 to realize a scan trajectory satisfying criteria discussed below.

Although two or all three of the robotic positioners 34, 36, and 38 might be part of the imaging system of FIG. 5, only one of the three would usually be in a given system. For example, the positioner 34 could be used to determine a scan trajectory by moving source 10 relative to object 12 and detector 14, both of which remain stationary. In that example, there would not be positioners 36 and 38.

The process for generating a backprojection of each x-ray line through a point x is described in conjunction with the mathematics used to recover the function f(x), wherein items (a–e) below provide the backdrop against which item (f) is developed. In item (f), the invention uses the inversion formula to recover the function f(x):

definition of the x-ray transform of function f and its relationship to cone beam data;

backprojection of each line through a point x rewritten as a convolution;

introduction of a Riesz potential;

definition an elliptic pseudo-differential operator;

backprojection of cone beam data shown to be a convolution of $R_1$, with f(x);

describe an inversion formula as a recovery of function f from the x-ray transform of function f using the pseudo-differential operator and $R_1$.

FIG. 3 illustrates an object to be imaged defined in terms of its x-ray attenuation coefficient f(x,y,z). FIG. 4 illustrates a projection of the object 0 onto a planar surface. The measured cone beam projection data then corresponds to a line integral of this function over the radial direction. The line integrals represent the object's density and are parametrized by points $\vec{x}$ on a line and a direction vector $\vec{\theta}$ associated with respective points $\vec{x}$. The measured cone beam projection data then corresponds to a line integral of this function over the radial direction, written as $$Xf(\vec{x}, \vec{\theta}) \equiv \int_{-\infty}^{\infty} f(\vec{x} + r\vec{\theta}) dr \qquad (0.1)$$

and is referred to as the x-ray transform of function f. The x-ray inversion formula, to be described herein, requires all line integrals through the imaging object. For example, referring to FIG. 4, a continuously sampled helical path would generate complete x-ray data in the limit, as the helical pitch L approaches zero, the cone half angle approaches π/2 and as the detector dimensions H and W approach infinity. In practical use, the x-ray data is sampled discretely, which forces numerical quadrature of the integrals in the inversion formula. Optimal quadrature techniques depend upon the scan path, cone angle, and detector size.

Each line is backprojected through the point x and the backprojection is rewritten as a convolution $$1/2 \int_{S^2} f(\vec{x}, \vec{\theta}) d\vec{\theta} = \int_{S^2} \int_{r=0}^{\infty} f(\vec{x} + r\vec{\theta}) dr d\vec{\theta} \qquad (0.2)$$

$$\int_{S^2} \int_{r=0}^{\infty} \frac{f(\vec{x} + r\vec{\theta})}{r^2} r^2 dr d\vec{\theta}$$

$$\int_{\mathbb{R}^n} \frac{f(\vec{x} + \vec{y})}{|\vec{y}|^2} d\vec{y}$$

Riesz potentials are known as a class of potential functions having special Fourier transformations and take the form $$R_\alpha(\Phi) |\Phi|^{-(n-\alpha)} \qquad (0.3)$$

where n is the spatial dimension and, as applied to this problem in $\mathbb{R}^3$, $$R_1(\vec{x}) = 1/(\pi|\vec{x}|^2)$$

so that $$R_1(\vec{\xi}) = 1/(|\vec{\xi}|) \quad (0.4)$$

The elliptic pseudo-differential operator $\Lambda$ is defined as $$\Lambda \equiv \frac{1}{2\pi}\sqrt{-\Delta} \quad (0.5)$$

It is apparent that $\Lambda$ is a filter that emphasizes high frequency components of the function f. It also is seen that convolving a function f with $R_1$ is the inverse of applying $\Lambda$ to the function f. When equations (0.4) and (0.2) are compared, it is seen that the backprojection of cone beam data as a convolution of $R_1$ with function f is written as $$\frac{1}{2\pi}\Lambda \int_{S^2} Xf(\vec{x},\vec{\theta})d\vec{\theta} = \Lambda(R_1 * f)(\vec{x}) = f(\vec{x}) \quad (0.6)$$

The function f is recovered from the x-ray transform of the function f, i.e., $Xf(x,\theta)$, by using operator $\Lambda$ and Riesz potential $R_1$, thereby obtaining the inversion formula $$\frac{1}{2\pi}\Lambda \int_{S^2} Xf(\vec{x},\vec{\theta})d\vec{\theta} = \Lambda(R_1 * f)(\vec{x}) = f(\vec{x}) \quad (0.7)$$

This inversion formula is interpreted as including in sequence, a backprojection step and a filtering step, in contrast to accepted reverse order of these steps. Moreover, the backprojecting portion of the inversion formula (0.7) smoothes the image, while filtering with $\Lambda$ emphasizes high frequency components.

The present invention thus provides a method and apparatus in which inversion values are calculated directly from respective cone beam measurements, providing computational efficiency. As used herein, "directly calculating" and the like refer to backprojecting measured imaging data and filtering to provide an accurate 3D image, without the necessity of computing radon data (that is, 2D planar integrals of the object's linear attenuation coefficient) from the measured data. Further, the present invention provides for an accurate image, that is without artifacts known to be present in approximation methods based on 2D reconstructions.

The technique of the present invention has a number of advantages over the prior art. The step of generating inverted Radon data from measured x-ray data is eliminated, thereby significantly reducing reconstruction time. The step of backprojecting x-ray data on the fly substantially reduces the lag time between the end of data collection and image generation. In general, the computational demands for image reconstruction process steps are reduced.

Thus, while various embodiments of the present invention have been illustrated and described, it will be appreciated to those skilled in the art that many change and modifications may be made there unto without departing from the spirit and scope of the invention.

What is claimed is:

1. A method of imaging an object comprising the steps of:
    applying imaging energy in the form of a cone beam from a source to the object;
    detecting imaging energy that has passed through the object by use of a detector;
    scanning the object with the imaging energy such that a detector collects measured image data in the form of cone beam measurements;
    calculating inversion values directly from respective cone beam measurements; and
    supplying an image of the object based on the calculated inversion values.

2. The method of claim 1 wherein the step of calculating inversion values includes the step of backprojecting the cone beam measurements.

3. The method of claim 1 wherein the step of calculating inversion values further includes the step of filtering the cone beam measurements so as to emphasize high frequency components.

4. The method of claim 1 wherein the step of backprojecting the cone beam measurements precedes the step of filtering the cone beam measurements.

5. The method of claim 2 wherein the inversion values are $$\frac{1}{2\pi}\Lambda \int_{S^2} Xf(\vec{x},\vec{\theta})d\vec{\theta} = \Lambda(R_1 * f)(\vec{x}) = f(\vec{x}),$$

where $R_1(\vec{x}) = 1/(\pi|\vec{x}|^2)$, and $\vec{x}$ is a point, $\vec{\theta}$ is a direction vector associated with $\vec{x}$, and $Xf(\vec{x},\sqrt{\theta})$ is an x-ray transform of $\vec{x}$.

6. The method of claim 5 wherein the step of backprojecting the cone beam measurements is performed while cone beam measurements are being collected.

7. The method of claim 6 wherein the step of backprojecting the cone beam measurements includes interpolation to a Cartesian grid.

8. The method of claim 7 wherein the step of interpolation to a Cartesian grid includes Rf is a convolution of $R_1$ with a function f for a point x on a line integral cone beam measurement of an object's density, and N is an angle, wherein $$\frac{\Lambda}{2}\int_0^\infty Rf(x \cdot (\cos\phi, \sin\phi), (\cos\phi, \sin\phi))d\phi = f(x).$$

9. The method of claim 8 wherein the scanning step is accomplished by moving the source in a scanning trajectory relative to the object.

10. The method of claim 8 wherein the scanning step is accomplished by moving the object in a scanning trajectory relative to the source.

11. A system for imaging an object comprising:
    a source for applying imaging energy to the object, the source being moveable relative to the object;
    a detector for detecting imaging energy that has passed through the object;
    a calculator for calculating direct inversion values corresponding to respective cone beam measurements, wherein the calculated direct inversion values include the calculation of backprojecting values and filtering values such that the filter values emphasize high frequency components, and the calculator calculates the backprojection values before calculating the filter values;
    a positioner scanning the object with the imaging energy such that the detector collects measured image data; and a display supplying an image of the object based on the calculated measured image data and the calculated direct inversion values.

12. The system of claim 11 wherein the calculator calculates backprojecting values while cone beam measurements are being collected.

13. The system of claim 11 wherein the detector is an area detector and the source is a point source.

14. The system of claim 11 wherein the positioner moves the source in a scanning trajectory relative to the object.

15. The system of claim 11 wherein the positioner moves the object in a scanning trajectory relative to the source.

16. The system of claim 11 wherein the detector is an area detector and the source is a point source.

* * * * *